United States Patent [19]

Ishimaru et al.

[11] Patent Number: 4,987,067
[45] Date of Patent: Jan. 22, 1991

[54] MALTOOLIGOSACCHARIDE DERIVATIVES AND REAGENTS FOR DETERMINATION OF AMYLASE ACTIVITY

[75] Inventors: Katsutoshi Ishimaru, Fukuoka; Akira Shimada, Moriguchi; Shinichi Teshima, Tsuruga; Yuzo Hayashi, Takarazuka, all of Japan

[73] Assignees: Yoshitomi Pharmaceutical Industries, Ltd.; Toyo Boseki Kabushiki Kaisha, both of Osaka, Japan

[21] Appl. No.: 279,105

[22] Filed: Dec. 2, 1988

[30] Foreign Application Priority Data

Dec. 11, 1987 [JP] Japan ................. 62-314379

[51] Int. Cl.$^5$ ................. C12Q 1/40; C07H 15/24
[52] U.S. Cl. ........................ 435/22; 435/14; 536/18.1
[58] Field of Search ........... 536/6, 18.1; 435/14, 435/22

[56] References Cited

U.S. PATENT DOCUMENTS 4,649,108  3/1987  Blair ..................... 435/8
4,709,020  11/1987  Rauscher et al. ............ 536/17.8

Primary Examiner—Sam Rosen
Attorney, Agent, or Firm—Wenderoth, Lind & Ponack

[57] ABSTRACT

Maltooligosaccharide derivatives represented by the general formula:

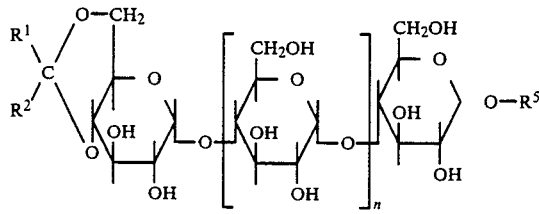

wherein at least one of $R^1$ and $R^2$ denotes a radical represented by: $R^3-S(O)_m-R^4$ or $R^3-CO-R^4$, and the rest of them denotes hydrogen atom, an alkyl radical containing 1 to 6 carbon atoms or a phenyl radical, in which $R^3$ is an alkyl radical containing 1 to 5 carbon atoms, $R^4$ is an alkylene radical containing 1 to 5 carbon atoms, and $m$ is 1 or 2, $R^5$ denotes a substituted or non-substituted phenyl radical, and $n$ denotes an integer of 1 to 8; and reagents comprising the maltooligosaccharide derivatives.

6 Claims, No Drawings

MALTOOLIGOSACCHARIDE DERIVATIVES AND REAGENTS FOR DETERMINATION OF AMYLASE ACTIVITY

BACKGROUND OF THE INVENTION

1. Field of the Invention:

This invention relates to novel maltooligosaccharide derivatives and to reagents for the determination of α-amylase activity wherein the maltooligosaccharide derivatives are used as substrates.

2. Prior Art Statement

Various diseases are diagnosed by determining the activity of α-amylase contained in body fluids such as pancreatic juice, urine, etc. For the determination of the activity of α-amylase, for example, a method that utilizes maltooligosaccharides such as maltotetraose, maltopentaose, maltohexaose, etc. as substrates is known. According to this method, a maltooliosaccharide and α-glucosidase are acted upon samples containing α-amylase to liberate glucose from the substrate, and the quantities of the glucose thus liberated are measured, whereby the activity values of α-amylase are found.

The glucose so produced is determined, for example, by a quantitative measurement method that utilizes a glucoseoxidase/peroxidase/pigment series, another measurement method that utilizes a hexokinase/phosphoglucomutase/glucose-6-phosphate dehydrogenase/NADH series, etc. Since α-glucosidase is difficult to act on tetrasaccharides or higher oligosaccharides such as maltopentaose and acts satisfactorily on trisaccharides or lower oligosaccharides such as maltose, maltotriose, etc., the activity of α-amylase can be determined by using the aforementioned substrate and measuring the glucose. However, though slightly, α-glucosidase acts on maltopentaose as substrate and because of this, elevated blank values are measured, which leads to larger errors in measurements. Owing to the decomposition action of α-glucosidase to the substrate, it is not preferred to prepare a one-part liquid reagent containing both α-glucosidase and the substrate because its reagent stability is impaired Another determination method of the activity is proposed, which uses substrates wherein a phenyl group, a naphthyl group or their derivatives are bonded to the reducing ends of maltooligosaccharides as a glycon Examples of such substrates include p-nitrophenylmaltopentaoside (Japanese Patent Publication No. 57-53079 (1982)), p-nitrophenylmaltohexaoside (Japanese Patent Publication No. 57-53079 (1982)), p-nitrophenylmaltoheptaoside (Japanese Patent Unexamined Publication No. 54-51892 (1979)), 2,4-dichlorophenylmaltopentaoside (Japanese Patent Unexamined Publication No. 56-35998 (1981)),etc. When these substrates are used, aglycons are liberated, and optical measurement of the liberated aglycons, e.g. p-nitrophenol permits easy determination of the activity of α-amylase This method also has the defect that α-glucosidase acts on the substrates, though slightly, and consequently, elevated blank values are measured Because of the substrate-decomposing action of α-glucosidase, it is difficult to prepare a onepart liquid type reagent containing at once α-glucosidase and the substrates, as in the case of the foregoing method of determining glucose.

In order to remove the drawbacks, there is provided a method of employing substrates of such type that the hydroxyl group at the 6-position of the non-reducing terminal glucose of maltooligosaccharides is modified For instance, Japanese Patent Unexamined Publication No. 60-237998 (1985) discloses maltooligosides as substrates wherein OH group at 6-position of the non-reducing terminal glucose of maltooligosaccharides is substituted, for example, by a halogen atom, —OR, —OCOR, —OSO$_2$R or —NHR (wherein R is alkyl, phenyl, pyridyl radicals, etc.) and the reducing terminal glucose of it is bonded with a substituted or non-substituted phenyl group as aglycon. The OH group at the 6-position of the non-reducing terminal glucose being substituted, the substrates do not undergo any decomposition by means of α-glucosidase.

However, such substrates having a substituent introduced solely at the 6-position are difficult to synthesize and are produced only in low yields.

Japanese Patent Unexamined Publication No. 60-54395 (1985) discloses maltooligosides for use as substrates, wherein 0H groups at the 4- and 6-positions of the non-reducing terminal glucose of maltooligosaccharides are substituted by an alkyl group, an alkoyl group or a phenyl group and the reducing terminal glucose of it is bonded with aglycon. Because of the fact that OH groups at the 4-position and 6-position of the nonreducing terminal glucose are substituted, the substrates are little susceptible to being decomposed by α-glucosidase The substrates are, however, poorly water-soluble, having two OH groups substituted, and hence it is impossible to prepare a high concentration solution Therefore, it is disadvantageous in that the substrates cannot be dissolved to a sufficient concentration for the determination of c-amylase activity.

SUMMARY OF THE INVENTION

The present invention is aimed at resolving the drawbacks of the aforesaid known substrates for the determination of α-amylase activity as well as the defects in known reagents for the determination of α-amylase activity. It is an essential object of this invention to provide novel maltooligosaccharide derivatives which do not undergo the action of an adjuvant enzyme like α-glucosidase under conditions of one-part liquid system of the substrate and the adjuvant enzyme, are readily synthesized and are superior in water solubility. Another object of the invention is to provide reagents capable of determining the activity of α-amylase in a body fluid with good precision and in a simple procedure by the use of the novel maltooligosaccharide derivatives as substrates.

This invention resides in:

(1) maltooligosaccharide derivatives represented by the formula (I):

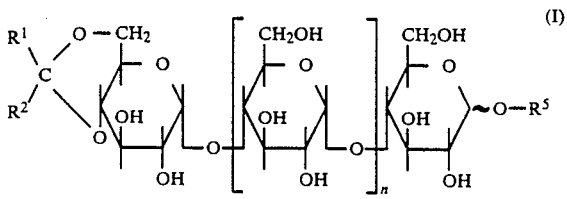

wherein at least one of R$^1$ and R$^2$ denotes radicals represented by: R$^3$—S(O)$_m$—R$^4$ or R$^3$—CO—R$^4$ (R$^3$ is an alkyl radical containing 1 to 5 carbon atoms, R$^4$ is an alkylene radical containing 1 to 5 carbon atoms, and m is 1 or 2) and the rest of R$^1$ and R² denotes hydrogen atom, an alkyl radical of 1 to 6 carbon atoms or a phenyl radical; R⁵ denotes a substituted or non-substituted phenyl radical; and n is an integer of 1 to 8 [hereinafter referred to as maltooligosaccharide derivatives (I)]: and (2) reagents for the determination of α-amylase activity comprising the maltooligosaccharide derivatives (I).

DETAILED DESCRIPTION OF THE INVENTION

The matooligosaccharides constituting the skeletons of the maltooligosaccharide derivatives (I) as substrates to be used in this invention are composed of three to ten saccharides [corresponding to n=1–8 in formula (I)]. Examples of the maltooligosaccharides include maltotriose, maltotetraose, maltopentaose, maltohexaose, maltoheptaose, etc. Among them, preferred are maltotetraose, maltopentaose, maltohexaose and maltoheptaose.

R¹ and R² which are substituent radicals of the nonreducing terminal glucose of each maltooligosaccharide may be the same or different from each other.

At least one of R¹ and R² denotes radicals of the formula:

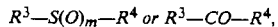

and the rest of them denotes hydrogen atom, an alkyl radical containing 1 to 6 carbon atoms (e.g. methyl, ethyl, propyl, isopropyl, butyl, tert.-butyl, pentyl, hexyl, etc.) or a phenyl radical. R⁵ denotes a substituted or non-substituted phenyl radical, and n is 1 to 8. R³ denotes an alkyl radical containing 1 to 5 carbon atoms (e.g. methyl, ethyl, propyl isopropyl, butyl, tert.-butyl, pentyl, etc.), R⁴ is an alkylene radical of 1 to 5 carbon atoms (e.g. methylene, ethylene, trimethylene, propylene, butylene, tetramethylene, pentamethylene, etc.), and m is 1 or 2.

The radicals represented by R³—S(O)$_m$—R⁴ include, for example, methylsulfinylethyl, ethylsulfinylethyl, methanesulfonylethyl, ethanesulfonylethyl, etc. The radicals represented by R³—CO—R⁴ include, for example, 2-ketopropyl, 2-ketobutyl, 3-ketobutyl, 2-ketopentyl, 3-ketopentyl, 4-ketopentyl, etc.

R⁵ corresponding to the aglycon of modified maltooligosides is a substituted or non-substituted phenyl radical. R⁵ may be bonded to the OH group at the 1-position of the nonreducing terminal glucose in either α-type or β-type. The substituted phenyl radical signifies a phenyl radical having, as a substituent, a halogen atom, a hydroxy group, an alkyl radical of 1 to 6 carbon atoms, an alkoxy radical, an alkoxycarbonyl radical, a nitro group, etc., namely, a phenol residue. Substituted phenols capable of forming such residue include, for example, chlorophenol, dichlorophenol, hydroxyphenol, alkylphenols, alkoxyphenols, hydroxybenzoic acid, nitrophenol, halogenated nitrophenols, alkylated nitrophenols, alkoxylated nitrophenols, nitrated hydroxy benzoic acid, dinitrophenol, etc. Particularly, preferred are phenols having at least one nitro group, for example, 4-nitrophenol, 2-chloro-4-nitrophenol, 2,6-dichloro-4-nitrophenol, 2-fluoro4-nitrophenol, 2,6-difluoro-4-nitrophenol, 2-bromo-4-nitrophenol, 2,6-dibromo-4-nitrophenol, 2-nitrophenol, 2-hydroxy-4-nitrophenol, 3-hydroxy-4-nitrophenol, etc.

The maltooligosaccharide derivatives (I) as substrates according to this invention are novel compounds and can be produced by reacting a compound of the formula (II) below and a carbonyl compound represented by the formula (III-1) below or an acetal compound of the formula (III-2) below which is an acetal of the carbonyl compound.

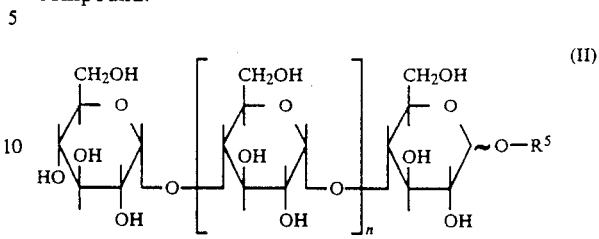

(wherein R⁵ and n have the same meanings as above)

or

(wherein R¹ and R² have the same meanings as above, and R⁶ and R⁷ represent the same or different lower alkyl radicals).

The lower alkyl radicals represented by R⁶ and R⁷ of the formulae (III-1) and (III-2) have preferably 1 to 10 carbon atoms, and there are exemplified methyl, ethyl, propyl, isopropyl, butyl, isobutyl, tert.-butyl, pentyl, isopentyl, iso-hexyl, etc.

The aforesaid reaction is generally carried out in a non-reactive solvent which includes, for example, dimethylformamide, dimethylsulfoxide, ethylene-glycol dimethylether, etc. If necessary, the compounds (III-1) or (III-2) per se are sometimes employed as a solvent The reaction temperature is not particularly limited, but is recommended to be usually in a range of from 0° C. to the boiling point of a solvent, more preferably, of from 40° to 100° C. Further, it is effective to conduct reflux heating under reduced pressure or to react while evaporating off by-product alcohols. A catalyst for accelerating the reaction, for example, a small amount of pure sulfuric acid, hydrogen chloride, p-toluenesulfonic acid or zinc chloride anhydride may be sometimes employed According to the foregoing production method, it is possible to bond a protecting cyclic acetal radical selectively to the non-reducing terminal glucose residue of the maltooligosaccharide. Hasegawa et al's research report on saccharide cyclic acetals [Carbohyd. Res., 29, 209 (1973)] and other reports have presented a method of bonding a cyclic acetal selectively to OH groups at the 4-position and 6-position of the glucose of a monosaccharide. However, as far as nucleus-substituted phenyl maltooligosides, which are of higher molecular weight are concerned, the method of bonding a cyclic acetal selectively to the 4- and 6-positions of the non-reducing terminal glucose residue is novel and highly useful.

The compounds (II) as a starting material, namely, nucleus-substituted phenyl maltooligosides can be synthesized by the reaction of nucleus-substituted aromatic compounds and maltooligosaccharides in a usual procedure. In a chemical procedure, the nucleus-substituted phenyl maltooligosides can be synthesized by acetylating the maltooligosaccharides, bonding the resulting acetylated maltooligosaccharides with the nucleus-substituted aromatic compounds, and subsequent deacetylation (cf. Lectures on Experimental Chemistry, 24, 304 (1958)). According to biochemical procedure, the nucleussubstituted phenyl maltooligosides can be synthesized by reacting cyclodextrin, glycosyltransferase-substituted aromatic compounds and soluble starches (or o-cyclodextrin or white dextrin).

For instance, methylthioethylidene 2-chloro-4-nitrophenyl-β-maltopentaoside is obtained by acting methylthioacetaldehyde dimethylacetal with 2-chloro-4-nitrophenyl-β-maltopentaoside in the presence of a slight amount of acidic catalyst.

The reagents for determination of α-amylase activity of this invention contain the aforesaid maltooligosaccharide derivatives (I) as substrates usually together with an enzyme series (adjuvant enzyme) combined appropriately by α-glucosidase, glucoamylase and β-glucosidase and, if necessary, other additives.

The origin of α-glucosidase to be used as the reagents for determination of α-amylase activity of this invention is not particularly limited. The α-glucosidase available from animals, plants and microorganisms can be employed Notably, α-glucosidase originated from yeast can be employed satisfactorily in respect that it acts well on maltooligoside or lower glycosides whereas it is difficult to act on maltotetraoside or higher glycosides and that the specificity of aglycons is broad.

The origins of β-glucosidase and glucoamylase to be used as the reagents for determination of α-amylase activity of this invention are not particularly limited, either. For example, β-glucosidase available from almond and glucoamylase available from lysopsdelemer can be used satisfactorily.

The determination of α-amylase activity by means of the reagents for determination of α-amylase activity of this invention is carried out, for example, as follows: Samples containing α-amylase are acted on the reagents for determination of α-amylase activity. In case of the substrate having aglycon bonded in α-type (α-type substrate), α-glucosidase and/or glucoamylase are used as an adjuvant enzyme system. In case of the substrate having aglycon bonded in β-type (β-type substrate), α-glucosidase and/or glucoamylase and β-glucosidase are used as an adjuvant enzyme system.

In the determination method using the reagents for determination of α-amylase activity of this invention, the decomposition reaction scheme of the substrates will be explained referring to the example of 3-ketobutylidene 2-chloro-4-nitrophenyl-β-maltopentaoside.

(i) 3-ketobutylidene 2-chloro-4-nitrophenyl-β-maltopentaoside
    ↓ α-amylase
2-chloro-4-nitrophenyl-β-maltoside + 3-ketobutylidenetriose (ii) 2-chloro-4-nitrophenyl-β-maltoside + 3-ketobutylidenetriose
    ↓ α-glucosidase and/or glucoamylase
2-chloro-4-nitrophenyl-β-glucoside + glucose + 3-ketobutylidenetriose (iii) 2-chloro-4-nitrophenyl-β-glucoside
    ↓ β-glucosidase
2-chloro-4-nitrophenol + glucose The phenolic compound (2-chloro-4-nitrophenol in case of this example) liberated in such decomposition reaction is measured by a suitable means whereby α-amylase activity can be determined. In case where the liberated phenolic compound exhibits different absorption spectrum from its substrate, spectrum of the reaction mixture is directly taken. Where the phenolic compound liberated from its substrate shows nearly the same spectral absorption as the substrate, the phenolic compound is condensed oxidizingly with the chromogen of a coloring reagent, e.g. 4-aminoantipyrine and hydrogen peroxide in the presence of peroxidase thereby to measure its color development intensity For the determination of phenolic compound, either Rate assay method wherein the reaction by α-amylase is followed up consecutively or endpoint method wherein after the reaction is carried out for a predetermined time period, the reaction is stopped to carry out measurement, can be applied.

In the reaction by the enzymes contained in the reagents of this invention, glucoamylase has nearly the same functions as α-glucosidase. However, α-glucosidase acts well on maltotrioside or lower molecule glycosides, but is difficult to act on maltotetraoside or higher glucosides whereas glucoamylase acts on maltotetraoside or higher glucosides as well as maltotrioside or lower glucosides. For instance, when maltoheptaoside or higher molecule glucosides are used as a substrate, maltotetraoside or higher glucosides can sometimes be produced by the action of α-amylase. Such maltotetraoside or higher glucosides are difficult to be decomposed with α-glucosidase, but are readily decomposed to glucose unit by the use of glucoamylase. As a consequence, sensitivity of the measurement system is enhanced. The adjuvant enzyme system wherein α-glucosidase and glucoamylase coexist is utilized satisfactorily.

According to the reagents and determination method of this invention, α- or β-maltooligosides, i.e. maltooligosaccharide derivatives wherein OH groups at the 4- and 6-positions of the non-reducing terminal glucose are modified are utilized as substrates and consequently, it is possible to prepare and preserve a one-part liquid reagent containing the adjuvant enzyme such as α-glucosidase or glucoamylase and the substrate with little decomposition of the substrate by these enzymes. Hence, any rise in blank values of the reagents is suppressed and precise determination of α-amylase activity is permitted.

The maltooligosaccharide derivatives (I) as substrates of this invention are superior in water solubility since $R^1$ and $R^2$ in formula (I) are water-soluble groups and are readily synthesized, so that they can be provided inexpensively.

Moreover, the reagents of this invention permit continuous determination with the aid of automatic analyzer whereby determination of α-amylase activity can be conducted simply, conveniently and economically.

The invention will be hereinbelow described in more detail by way of examples.

Example 1-1 (Synthesis)

Preparation of 3-ketobutylidene 2-chloro-4-nitrophenyl-β-maltopentaoside:

In a 300 ml flask, 10 g of 2-chloro-4-nitrophenyl-β-maltopentaoside, 150 ml of 1,3-dimethyl-2-imidazolidinone, 110 mg of p-toluene sulfonic acid and 2.7 ml of 4,4-dimethoxy2-butanone were mixed into a homogeneous solution and stirred at room temperature for 24 hours. Weak basic ion exchange resin, 22 g, was incorporated and after stirring for 2 hours, the solution was filtered The filtrate solution was transferred to a 300 ml pear-shaped flask and condensed quickly on a rotary evaporator under reduced pressure (2 mmHg) while maintaining the external temperature at 85° C.

The residue, 13.9 g, was dissolved in 56 ml of distilled water and loaded on a column of 20 cm in the inside diameter which is packed with 48 l of "Sephadex G-25 Gel" dispersed in distilled water and underwent gel filtration by using distilled water as effluent The fraction rich in 3-ketobutylidene-2-chloro-4-nitrophenyl-β-maltopentaoside was collected and concentrated and hydro-extracted to give 3.8 g of pale yellow crystals. The crystals were dissolved in 10 ml of methanol, crystallized out by addition of 40 ml of diethylether under cooling and filtered followed by drying. A 3.0 g quantity of 3-ketobutylidene-2-chloro-4-nitrophenyl-β-maltopentaoside in white crystals was obtained (purity of 99% according to HPLC analysis), m.p. 188–192° C. NMR; δ value (splitting type, relative proton number)

2.2 (singlet line, 3)
2.9 (doublet line, 3)
3.2 - 4.2 (multiplet line, 31)
4.7 (singlet line, 14)
5 - 5.6 (multiplet line, 5)
7.3 (doublet line, J=9Hz, 1)
8.15 (double doublet line, J=3Hz, J=9Hz, 1)
8.21 (doublet line, J=3Hz, 1)

The singlet peak at 6 of 2.2 (3H) and the doublet peak at 67 of 2.9 (2H) are absorptions based on $CH_3CO-$ radical and $-COCH_2-$ radical respectively and respective one radical is present in one molecule of 3-ketobutylidene-2-chloro 4-nitrophenyl-β-maltopentaoside.

Examples 1-2 to 1-8 (Synthesis)

The following compounds are prepared according to the procedure of Example 1:

2-Ketobutylidene 2-chloro-4-nitrophenyl-β-maltopentaoside
2-Ketopropylidene 2-chloro-4-nitrophenyl-β-maltopentaoside
4-Ketopentylidene 2-chloro-4-nitrophenyl-β-maltopentaoside
Methylsulfinylethylidene 2-chloro-4-nitrophenyl-β-maltopentaoside
Ethylsulfinylethylidene 2-chloro-4-nitrophenyl-β-maltopentaoside
Methanesulfonylethylidene 2-chloro-4-nitrophenyl-β-maltopentaoside
Ethanesulfonylethylidene 2-chloro-4-nitrophenyl-β-maltopentaoside

Example 2 Comparative Example 1 (Reagent Determination Method)

Reagents having the following composition were prepared.
Composition of reagents:
50 mM Good Buffer (pH 7.0)
α-Glucosidase 80 U/ml
β-Glucosidase 10 U/ml
Substrate (see Table 1) 2 mM Immediately after the preparation of the reagents, after 10 minutes, 20 minutes and 30 minutes, the absorbance of each reagent at 400 nm was determined (3 ml of reagent sample; 37° C.). The variation in absorbance (variation in blank value with time) is shown in Table 1 given below.

TABLE 1

| | Substrate | On reaction initiation | After 10 min. | After 20 min. | After 30 min. |
|---|---|---|---|---|---|
| Example 2 | 3-ketobutyliden 2-chloro-4-nitrophenyl-β-maltopentaoside | 0.049 | 0.049 | 0.049 | 0.050 |
| Comp. Ex. 1 | 2-chloro-4-nitrophenyl-β-maltopentaoside | 0.251 | 0.273 | 0.293 | 0.323 |

From Table 1, it will be seen that the reagent of this invention containing the compound with modified non-reducing terminal as a substrate has lower blank values and causes little rise in the blank value with time, as compared with the comparative reagent containing, as a substrate, the compound whose non-reducing terminal is not modified.

Example 3-1 (Reagent Determination Method)

The reagent of the following composition was prepared. Composition of Reagent:
50 mM Good Buffer (pH 7.0)
α-Glucosidase 80 U/ml
β-glucosidase 10 U/ml
Glucoamylase 10 U/ml
Substrate (See Table 1) 2 mM With this reagent, variation in absorbance was determined in a similar manner to Example 2. A 3 ml quantity of the reagent was added to 50 ml of sample serum and allowed to stand for 5–6 minutes at 37° C. and thereafter, the variation in absorbance at 400 nm was determined and the change in absorbance per one minute which is an indication of amylase activity was calculated The variation in blank value of the reagent with time and the change in absorbance per minute are shown in Table 2 below.

Example 3-2 (Reagent Determination Method)

The reagent having the following composition was prepared:
Composition of Reagent
50 mM Good Buffer (pH 7.0)
α-Glucosidase 80 U/ml
β-Glucosidase 10 U/ml
Substrate (see Table 2) 2 mM By the use of the reagent, similar procedure to Example 3-1 was repeated and the results obtained are shown in Table 2 given below.

TABLE 2

|  | Substrate | On reaction initiation | After 10 min. | After 20 min. | After 30 min. | Change in absorbance | Note |
|---|---|---|---|---|---|---|---|
| Example 3-1 | 3-ketobutylidene 2-chloro-4-nitro-phenyl-β-malto-pentaoside | 0.051 | 0.051 | 0.051 | 0.052 | 0.157 | gluco-amylase added |
| Example 3-2 | 3-ketobutylidene 2-chloro-4-nitro-phenyl-β-malto-pentaoside | 0.050 | 0.051 | 0.051 | 0.051 | 0.123 | — |
| Comp. Ex. 2 | 2-chloro-4-nitro-phenyl-β-malto-pentaoside | 0.132 | 0.162 | 0.192 | 0.223 | 0.136 | gluco-amylase added |

Comparative Example 2

The reagent of the following composition was prepared:
Composition of reagent
  50 mM Good Buffer (pH 7.0)
  α-Glucosidase 80 U/ml
  β-Glucosidase 10 U/ml
  Glucoamylase 10 U/ml
  Substrate (see Table 2) 2 mM Using the reagent, the procedure of Example 3-1 was repeated and the results obtained are shown in Table 2.

As will be apparent from Table 2, the reagents of this invention (Examples 3-1, 3-2) have each low blank values and an extremely low rise degree of blank value with time, as compared with the reagent containing, as a substrate, the compound whose non-reducing terminal is not modified (Comparative Example 2). In Example 3-1, the measurement sensitivity is confirmed to be enhanced in comparison with Example 3-2, because glucoamylase is contained in the reagent in Example 3-1.

Comparative Example 3

An attempt was made to use the substrates listed below instead of the substrates in Example 3, but the former substrates were not dissolved in the reagents in Example 3 (excluding substrates in Example 3).
Benzylidene 2-chloro-4-nitrophenyl-β-maltopentaoside
Methylidene 2-chloro-4-nitrophenyl-β-maltopentaoside
Benzylidene 2-chloro-4-nitrophenyl-β-maltopentaoside
Isopropylidene 2-chloro-4-nitrophenyl-β-maltopentaoside

We claim:
1. A maltooligosaccharaide derivative represented by the general formula:

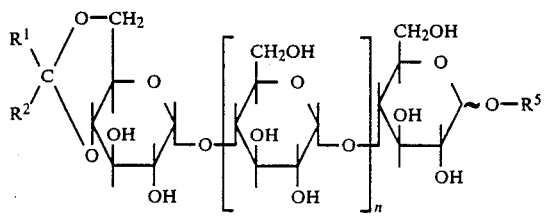

wherein at least one of $R^1$ and $R^2$ denotes a radical represented by: $R^3$—$S(O)_m$—$R^4$, and the remainder denotes a hydrogen, an alkyl radical containing 1 to 6 carbon atoms or a phenyl radical, in which $R^3$ is an alkyl radical containing 1 to 5 carbon atoms, $R^4$ is an alkylene radical containing 1 to 5 carbon atoms, and m is 1 or 2; $R^5$ denotes a phenyl radical unsubstituted or substituted by halogen, hydroxy, alkyl of 1 to 6 carbon atoms, alkoxy, alkoxycarbonyl or nitro; and n denotes an integer of 1 to 8.

2. The maltooligosaccharide derivative of claim 1 which is 3-ketobutylidene 2-chloro-4-nitrophenyl-β-maltooligopentaoside.

3. A reagent for the determination of α-amylase activity comprising a maltooligosaccharide derivative represented by the general formula:

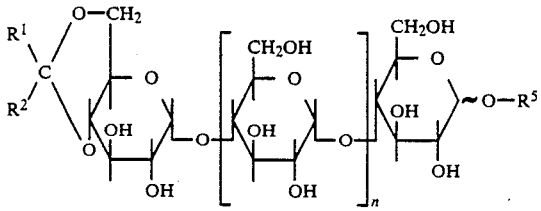

wherein at least one of $R^1$ and R denotes a radical represented by: $R^3$—$S(O)_m$—R or $R^3$—CO—$R^4$, and the remainder denotes a hydrogen, an alkyl radical containing 1 to 6 carbon atoms or a phenyl radical, in which $R^3$ is an alkyl radical containing 1 to 5 carbon atoms, $R^4$ is an alkylene radical containing 1 to 5 carbon atoms, and m is 1 or 2; $R^5$ denotes a phenyl radical unsubstituted or substituted by halogen, hydroxy, alkyl of 1to 6 carbon atoms, alkoxy, alkoxycarbonyl or nitro; and n denotes an integer of 1 to 8, and
an adjuvant enzyme.

4. The reagent for the determination of α-amylase activity as set forth in claim 3, wherein said maltooligosaccharide derivative is 3-ketobutylidene 2-chloro-4-nitrophenyl-β-maltooligo-pentaoside.

5. The reagent for the determination of α-amylase activity as set forth in claim 3, which further comprises α-glucosidase and/or glucoamylase and optionally, 62 -glucosidase.

6. The reagent for the determination of α-amylase activity as set forth in claim 5, wherein said maltooligosaccharide derivative is 3-ketobutylidene 2-chloro-nitrophenyl-62 -maltooligopentaside.

* * * * *

UNITED STATES PATENT AND TRADEMARK OFFICE
CERTIFICATE OF CORRECTION

PATENT NO. : 4,987,067

DATED : January 22, 1991

INVENTOR(S) : Katsutoshi ISHIMARU et al.

It is certified that error appears in the above-identified patent and that said Letters Patent is hereby corrected as shown below:

| | | |
|---|---|---|
| Column 1, | Line 19: | Amend "maltooliosaccharide" to "maltooligosaccharide"; |
| Column 1, | Line 60: | Insert ".(period)" following "measured"; |
| Column 1, | Line 62: | Amend "onepart" to "one-part"; |
| Column 2, | Line 1 : | Insert ".(period)" following "modified"; |
| Column 2, | Line 27: | Insert ".(period)" following "$\alpha$-glucosidase"; |
| Column 2, | Line 30: | Insert ".(period)" following "solution"; |
| Column 2, | Line 32: | Amend "c-amylase" to "$\alpha$-amylase"; |
| Column 3, | Line 11: | Amend "matooligosaccharides" to "maltooligosaccharides"; |
| Column 3, | Line 62: | Amend "2-fluoro4" to "2-fluoro-4"; |
| Column 5, | Line 13: | Amend "o-cyclodextrin" to "$\alpha$-cyclodextrin"; |
| Column 5, | Line 31: | Insert ".(period)" following "employed"; |
| Column 7, | Line 17: | Amend "4,4-dimethoxy2" to "4,4-dimethoxy-2"; |
| Column 7, | Line 21: | Insert ".(period)" following "filtered"; |
| Column 7, | Line 29: | Insert ".(period)" following "effluent"; |
| Column 7, | Line 48: | Amend "6" to "$\delta$"; |
| Column 7, | Line 49: | Amend "67" to "$\delta$"; |
| Column 8, | Line 56: | Insert ".(period)" following "calculated"; |
| Column 9, | Line 54: | Amend "maltooligosaccharaide" to "maltooligosaccharide"; |
| Column 10, | Line 2 : | Insert "or $R^3-CO-R^4$" between "$R^3-S(O)_m-R^4$," and "and"; |
| Column 10, | Line 42: | Amend "R" to "$R^2$"; |

UNITED STATES PATENT AND TRADEMARK OFFICE
CERTIFICATE OF CORRECTION

PATENT NO. : 4,987,067

DATED : January 22, 1991

INVENTOR(S) : Katsutoshi ISHIMARU et al.

It is certified that error appears in the above-identified patent and that said Letters Patent is hereby corrected as shown below:

Column 10, Line 43: Amend "R" to "$R^2$";

Column 10, Line 59: Amend "62" to "$\beta$";

Column 10, Line 64: Amend "62" to "$\beta$".

Signed and Sealed this

Sixteenth Day of March, 1993

Attest:

STEPHEN G. KUNIN

Attesting Officer

Acting Commissioner of Patents and Trademarks